United States Patent [19]

Yamamoto

[11] Patent Number: 4,828,704
[45] Date of Patent: May 9, 1989

[54] THIN-LAYER ROD FOR CHROMATOGRAPHY

[75] Inventor: Yojiro Yamamoto, Saitama, Japan

[73] Assignees: Cosmo Oil Company, Ltd.; Iatron Laboratories, Inc., both of Tokyo, Japan

[21] Appl. No.: 132,223

[22] Filed: Dec. 14, 1987

Related U.S. Application Data

[63] Continuation of Ser. No. 839,387, May 14, 1986, abandoned.

[30] Foreign Application Priority Data

Mar. 15, 1985 [JP] Japan .................................. 60-52696

[51] Int. Cl.$^4$ .......................................... B01D 15/08
[52] U.S. Cl. .................................... 210/635; 210/658; 210/198.3; 422/54; 422/70; 436/154; 436/162
[58] Field of Search ............ 214/635, 656, 658, 198.2, 214/198.3; 422/54, 70, 78; 436/154, 162

[56] References Cited

U.S. PATENT DOCUMENTS

| 3,387,710 | 6/1968 | Pogacar | 210/198.3 |
| 3,722,181 | 3/1973 | Kirkland | 210/198.2 |
| 3,795,313 | 3/1974 | Kirkland | 210/198.2 |
| 3,839,205 | 10/1974 | Ikumura | 210/198.3 |
| 4,295,968 | 10/1981 | Halpaap | 210/198.3 |
| 4,372,850 | 2/1983 | Okumura | 210/198.2 |
| 4,590,167 | 5/1986 | Gunther | 210/658 |

FOREIGN PATENT DOCUMENTS

| 2125428 | 12/1971 | Fed. Rep. of Germany ... | 210/198.3 |
| 2712113 | 9/1978 | Fed. Rep. of Germany ... | 210/198.3 |
| 2809137 | 9/1979 | Fed. Rep. of Germany ... | 210/198.3 |
| 2462183 | 2/1981 | France ............................. | 210/198.3 |

Primary Examiner—Ernest G. Therkorn
Attorney, Agent, or Firm—Sughrue, Mion, Zinn, Macpeak & Seas

[57] ABSTRACT

A thin-layer rod for thin-layer chromatography conducted by the use of a flame ionization detector, comprising a rodlike support and a stationary phase made of an adsorbent which is superposed on the rod-like support, with chemical modification made in at least part of the stationary phase.

13 Claims, 1 Drawing Sheet

THIN-LAYER ROD FOR CHROMATOGRAPHY

This is a continuation of application Ser. No. 839,387 filed May 14, 1986 now abandoned.

FIELD OF THE INVENTION

This invention relates to a thin-layer rod for chromatography, and more particularly to a thin-layer rod of high performance for thin-layer chromatography operated by the use of a flame ionization detector. The thin-layer rod of this invention uses a chemically modified adsorbent as part of a stationary phase thereof, by which it is enabled to effect affinity chromatography and provide a high degree of separation as compared with a conventional thin-layer rod. The accuracy of determination which is enjoyed by this thin-layer rod is not impaired by the chemical modification.

BACKGROUND OF THE INVENTION

Chromatography is a useful means of analysis which has found extensive utility in a variety of fields. It is classified broadly into several groups such as, for example, gas chromatography, column chromatography, thin-layer chromatography (TLC), and paper chromatography. TLC can further be classified into two major sub-groups, i.e., ordinary TLC using a plate having a stationary phase superposed in the form of a thin layer on a quartz glass plate, and TLC using a thin-layer rod having a stationary phase baked on a quartz glass rod. The present invention relates to a thin-layer rod for use in the TLC in the latter sub-group.

Chromatography is a method for separating a given sample into its components, detecting the components, and determining their amounts by utilizing differences the components exhibit in terms of the ratio, $R_f$, between the speed of movement of the component of interest and the speed of movement of the developer which is fixed by the ratio of the affinity a given component shows for the stationary phase to the affinity for the developer. The differences in $R_f$, therefore, enable separation of the components to be easily and sufficiently effected, based on the differences in affinity the components exhibit for the stationary phase. For the separation to be advantageously effected, the simple fact that the differences in affinity exist and that those differences in $R_f$ are large is not necessarily sufficient. The fact that the image of the chromatogram is not obscure but is clear and free from diffusion constitutes itself an essential requirement. If the image is obscure, the individual images of the components separated somewhat due to the differences in affinity still tend to overlap, barring the achievement of effective separation, detection, and determination of the components aimed at by the chromatography.

As one means of clarifying the differences in affinity of the components for the stationary phase and preventing the image of the chromatogram from being obscure, in the field of the column chromatography and the ordinary TLC using a thin-layer plate, the technique of chemically modifying the stationary phase by the treatment with a varying chemical substance has been utilized, as disclosed in U.S. Pats. Nos. 4,295,968 and 4,372,850.

In the ordinary TLC using a thin-layer plate, it is normal to effect the detection of the components and the determination of their amounts through measurement of the amounts of ultraviolet light absorbed by the components. This method may be suitable for qualitative analysis, but is not satisfactory for quantitative analysis. This is because the components of a given sample have different degrees of absorbance for the ultraviolet light, and, therefore, two equal degrees of absorbance exhibited by two components do not immediately mean that the concentrations of these two components are equal and, by the same token, the areas the components occupy in the chromatogram do not permit direct determination of the amounts of the components.

In contrast, the TLC conducted by the use of a flame ionization detector (FID) has the advantage that in the analysis of hydrocarbons, the areas occupied by the components in the chromatogram are available for direct determination of the amounts of the components because the responses of the detector are faithfully proportionate to the concentrations of the components by weight. It has been ascertained that even in the separation of higher hydrocarbons, the responses of the detector are faithfully proportionate to the weight concentrations. For the quantitative analysis of higher hydrocarbons, therefore, the thin-layer chromatography conducted by the use of a flame ionization detector (FID-TLC) proves to be a highly advantageous means. Unfortunately, the FID permits use of a thin-layer rod, but not the ordinary thin-layer plate, because of the restrictions imposed by the physical structure of the FID. Conventional thin-layer rods have not been chemically modified. Only thin-layer rods of a type having silica gel or alumina simply baked onto a quartz glass rod have been known to the art. These thin-layer rods are not very satisfactory in terms of the separating property, particularly because they have the disadvantage that the images of the chromatogram are subject to the phenomenon of tailing and lose clarity. Thus, they have not been fully suitable for the separation of higher hydrocarbons such as polycyclic aromatic hydrocarbons.

SUMMARY OF THE INVENTION

As a result of extensive studies devoted to further improving the separating properties of FID-TLC, there has now been achieved an improved thin-layer rod, thus resulting in the present invention.

An object of this invention, therefore, is to provide a thin-layer rod for FID-TLC excelling in performance and separating properties and overcoming substantially all problems in the ability to provide quantitative determinations.

More particularly, this invention provides a thin-layer rod for thin-layer chromatography conducted by the use of a flame ionization detector, which comprises a rodlike support and a stationary phase made of an adsorbent which is superposed on the rodlike support, with chemical modification made in at least part of the stationary phase.

Other features and advantages of the present invention will become more apparent to those skilled in the art as the disclosure is made in the following description of preferred embodiments of this invention and by reference to the accompanying drawings.

BRIEF DESCRIPTION OF THE DRAWINGS

FIGS. 2A and 2B represent chromatograms obtained in Comparative Experiments 5 and 6, respectively described below. FIG. 3 represents a chromatogram obtained in Example 5 described below. FIG. 4 represents a chromatogram obtained in Example 6 described below.

DETAILED DESCRIPTION OF THE INVENTION

Figure 1:
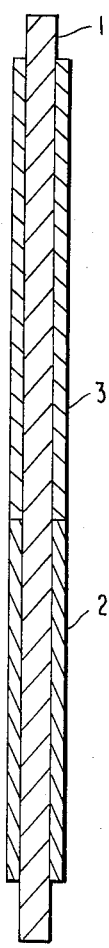
FIG. 1 shows a longitudinal cross-section illustrating the construction of a thin-layer rod according to the present invention.

One means of ensuring thorough separation of the components of a sample in a chromatographic analysis resides in using a long stationary phase. In TLC, however, the stationary phase to be used has its length limited to a fixed magnitude because of the restrictions imposed by the physical structure of the apparatus. It becomes necessary, therefore, to effect clear separation of the images of the components by the use of a stationary phase of a limited length. The salient cause for the obscurity of the images of a chromatogram resides in the fact that the images undergo the phenomenon of tailing. If the tailing could be effectively prevented, then even two close images would be clearly distinguished from each other and effective separation, detection, and determination of numerous components would be obtained by the use of a stationary phase of a limited length.

For separation of components which are extremely difficult to separate, a means of broadening the differences of $R_f$ is as important as any other means. In the ordinary analysis, however, a device for obtaining a clear image free from the phenomenon of tailing is still more important.

Among the conventional thin-layer rods used for thin-layer chromatography, there is counted a version which comprises a rodlike support such as quartz glass rod and a stationary phase made of such adsorbent as silica gel or alumina which is superposed on the rodlike support. Silica gel, for example, used as the adsorbent has on the surface thereof what is called "silanol" which is a hydroxyl group linked to a silicon atom. Since this silanol group exhibits varying degrees of affinity for different compounds, it manifests an effect of some measure upon the separation of various compounds. It is, however, known that the presence of a silanol group promotes the phenomenon of tailing of the image. This problem is associated not only with silica gel, but also with alumina and other known adsorbents which form the stationary phase in the thin-layer rod for chromatography. For the prevention of the phenomenon of tailing, the idea of chemically modifying the silanol group by the reaction of this group with a various compound has been conceived. In fact, this idea has already been embodied in the column chromatography and the ordinary TLC operated by the use of a thin-layer plate (as disclosed, for example, in U.S. Pat. Nos. 4,295,968 and 4,372,850).

This method has never been tried in FID-TLC, for the following reason. In the thin-layer rod for use in the FID-TLC, the stationary phase of an adsorbent is required to be adhered to the quartz rod by baking instead of being simply applied thereof, because a stationary phase formed by such simple application has the possibility of being peeled off the quartz rod by the heat of the hydrogen flame being used during the course of analysis. Unfortunately, the chemically modified adsorbent does not withstand the work of baking. To make the matter worse, in FID, the compound used for the chemical modification itself forms ions, and consequently causes an error in the determination.

For the improvement of the thin-layer rod for use in the FID-TLC, thereofre, it is necessary for the thin-layer rod to possess a chemically modified stationary phase incapable of being peeled even on exposure to the heat used by the FID and for the chemical modification to be incapable of causing an error in the determination.

As one means of solving the difficulty, the inventor has drawn an inference that it suffices to use a thin-layer rod which has a chemically modified stationary phase on the development-starting side thereof and a conventional stationary phase in the remaining part thereof. To be specific, the thin-layer rod of the present invention comprises a chemically modified separation part whose function is to effect clear separation, a further part (detection part) whose function is to receive images so separated, promote the separation further to a certain extent, and detect the separated components.

The thin-layer rod of the present invention cannot entail the problem of erroneous measurement because its detection part is not different from the conventional thin-layer rod. Further, it does not very easily suffer from the phenomenon of tailing because the part for receiving the images already separated clearly in the separation part and possessing a hydroxyl group, a silanol group, etc., is short. Thus, by the thin-layer rod of this invention, a clear chromatogram is obtained.

The construction of the thin-layer rod of the present invention is illustrated in FIG. 1. FIG. 1 is a figure illustrating a longitudinal cross-section of the thin-layer rod of this invention as a model. In this figure, 1 represents a rodlike support such as, for example, a quartz glass rod, 2 represents a separation part formed of a chemically modified stationary phase, and 3 represents a detection part formed of a conventional stationary phase. The lower side of the thin-layer rod as shown in the figure constitutes the side for starting the development.

The thin-layer rod for chromatography provided by the present invention will be described more specifically below. The thin-layer rod of the present invention comprises a rodlike support and a stationary phase formed of adsorbent which is superposed on the rodlike support and has at least part of the stationary phase including the development starting side thereof chemically modified. This thin-layer rod is intended for use in thin-layer chromatography which is conducted by the use of a flame ionization detector.

The rodlike support and the adsorbent to be used in the chromatographic thin-layer rod of this invention are not different from their conventional counterpypes. The fixation of the adsorbent on the rod-like support can be effected by the conventional method. Typically, the rodlike support has a diameter approximately in the range of from 0.3 to 3 mm and a length approximately in the range of from 10 to 20 cm. As the rodlike support, a rodlike member made of a heat-resistant and chemically stable material such as, for example, quartz, glass, or ceramics can be effectively used. As the adsorbent, a heat-resistant and chemically stable inorganic adsorbent such as, for example, silica gel, alumina, porous glass powder, diatomaceous earth, or magnesium silicate can be used. The deposition of the adsorbent on the rodlike support is accomplished, for example, by preparing a slurry from the adsorbent in a powdered form and a solvent such as acetone or ethanol, immersing the rod-like support in the slurry or applying the slurry on the rodlike support, then drying the rod-like support wet with the slurry, and sintering the applied slurry thereafter. Suitably, the thickness of the layer of the adsorbent so deposited on the rodlike support is approximately in the range of from 10 to 200 μm. A chromatographic thin-layer rod of the construction described above which is not yet chemically modified is readily available in the market.

For the purpose of this invention, this chromatographic thin-layer rod which has not been chemically modified has its stationary phase entirely, or the development starting side thereof, chemically modified. This chemical modification can be accomplished, for example, by treating the stationary phase made of the adsorbent layer with an organic silane, or by first treating the stationary phase with a halogenating agent and subsequently treating it with a Grignard reagent, an organic lithium, or an organic amine. Examples of the organic silane are a halogenated organic silane and an organic alkoxysilane. It is believed that by this chemical modification, the groups such as silanol group and hydroxyl group which adhere at least to the surface layer of the layer of the adsorbent and which has adverse effects on the analysis are masked by a hydrocarbon group or a polar group-substituted hydrocarbon group. Now, the manner in which the chemical modification contemplated by the present invention is effected will be described more specifically below.

The stationary phase of the separation part in the thin-layer rod of the present invention is desired to be chemically modified by the use of an organic silane. Particularly, an organic monosilane represented by formula (I),

$$X_n\text{—SiR}'_{3-n}\text{—R} \qquad (I)$$

is used advantageously for the chemical modification. In formula (I), X represents a halogen atom or an alkoxyl group, n represents 1, 2, or 3, R' represents an alkyl group such as methyl group or ethyl group, and R represents a monovalent hydrocarbon group or a monovalent polar group-substituted hydrocarbon group possessing a polar substituent (such as, for example, an amino group, a cyano group, a nitro group, a sulfonic acid group, or a carboxyl group). Specific examples of the polar group-substituted hydrocarbon group include polar group-substituted alkyl groups (such as an amino-alkyl group, a cyano-alkyl group, a nitro-alkyl group, a sulfo-alkyl group, and a carboxy-alkyl group) and monovalent nitro-aromatic groups. The chemical modification occurs by the fact that the hydrogen atom of the silanol group or hydroxyl group in the adsorbent reacts with the substituent X in formula (I) and consequently gives rise to a hydrogen halogenide or an alcohol. Desirably, X represents chlorine atom, methoxy group, or ethoxy group, R' represents a lower alkyl group having from 1 to 6 carbon atoms such as methyl group, R represents a monovalent hydrocarbon group having from 1 to 20 carbon atoms (such as, for example, an alkyl group, an alkenyl group, an aromatic group-substituted alkyl group, or an aromatic group), the alkyl group of the polar group-substituted alkyl group (such as, for example, an amino-alkyl group, a cyano-alkyl group, a nitro-alkyl group, a sulfo-alkyl group, and a carboxy-alkyl group) is an alkyl group having from 2 to 10 carbon atoms, and the monovalent nitro-aromatic group is a nitro-aromatic group having from 6 to 12 carbon atoms. Specific examples of the substituent R are 3-amino-propyl, 3-cyano-propyl, 3-nitro-propyl, nitro-phenyl, 3-sulfo-propyl, 3-carboxy-propyl, n-butyl, n-octadecyl, methyl, ethyl, n-octyl, phenyl, and phen-ethyl. Where the subscript n in formula (I) is 2 or 3, the unreacted portion of the substituent X remaining after the chemical reaction is converted to OH by hydrolysis and the produced OH group is treated by reaction with trimethylmonchlorosilane (for trimethylsilylation). To ensure that no unreacted silanol or hydroxyl group will survive in the stationary phase of adsorbent, the treatment with trimethylmonochlorosilane may be carried out even when the subscript n is 1. The hydrolysis and the trimethylsilylation mentioned above are not indispensable requirements.

Another method available for the chemical modification of the stationary phase of the separation part in the thin-layer rod of the present invention comprises first treating the stationary phase with a halogenating agent such as thionyl chloride, silicon chloride, or titanium chloride thereby converting the hydroxyl group or the OH moiety of the silanol group posessed by the adsorbent into a halogen group and subsequently treating the product with a Grignard reagent represented by the formula, RMgCl (wherein R has the same meaning as defined above with respect to formula (I)) or with an organic lithium compound represented by the formula RLi (wherein R has the same meaning as defined above with respect to formula (I)) or an organic amine represented by the formula RNH$_2$ (wherein R has the same meaning as defined above with respect to formula (I)), thereby converting the halogen group of the thin-layer rod into an R group or an NHR group. Even by this method, there can be produced a thin-layer rod equal to that which is chemically modified with an organic silane compound.

The stationary phase of the detection part is formed of alumina or silica gel, similarly to the conventional stationary phase. It is provided, however, that the separation part and the detection part should be smoothly connected to each other without fail. The thickness of the stationary phase on the thin-layer rod is required to be substantially constant.

In the thin-layer rod of the present invention, the proportion of the separation part preferably falls approximately in the range of about from 10 to 70% of the entire length of the stationary phase. More preferably, this proportion is selected to be approximately in the range of about from 30 to 60%. If the proportion of the separation part is less than 10%, the clarity of separation obtained by the thin-layer rod is not improved very much over that obtained by the conventional thin-layer rod. If the proportion exceeds 70%, the clarity of separation is notably improved but tends to be accompanied by the disadvantage that the detection part is so small as to barely effect desired analysis on compounds having R$_f$ values in the range of from 0.7 to 1.0 and, as a result, the thin-layer rod is useful only to a limited extent.

In the analysis of hydrocarbons, the thin-layer rod of the present invention more often than not shows R$_f$ values greater than the R$_f$ values recognized to be attained by the conventional thin-layer rod. Even when the proportion of the separation part is fixed at 30%, the thin-layer rod is amply capable of analyzing compounds showing $R_f$ values on the order of 0.2 when analyzed by utilizing the conventional thin-layer rod.

Now, a method useful for the manufacture of the thin-layer rod according to this invention is described below. The thin-layer rod of the present invention is not limited by the method adopted for its manufacture.

A commercially available thin-layer rod having adsorbent such as silica gel deposited fast thereon by baking is immersed in an anhydrous organic solvent such as dioxane or toluene having an organic monosilane of formula (I) dissolved in advance therein, and then the immersed thin-layer rod is left reacting thoroughly, such as by refluxing for a prescribed length of time. Although the time required for this reaction is variable with the reaction conditions, such as the temperature and the kind of the agent used for the chemical modification, a length of about 12 hours generally suffices. After completion of this reaction, the treated thin-layer rod is thoroughly washed with an organic solvent such as dioxane or toluene. Where the subscript n in formula (I) of the agent for chemical modification is 2 or 3, the OH group produced in consequence of the hydrolysis of the unreacted substituent X may be treated with trimethylmonochlorosilane. By the above reaction, the unreacted hydroxyl group or silanol group in the adsorbent of the stationary phase is simultaneously trimethylsilylated. Even when the subscript n is 1, the treatment with trimethylmonochlorosilane is desired to be performed for the purpose of ensuring that the hydroxyl group or silanol group is trimethylsilylated. This reaction proceeds rapidly. For example, this reaction thoroughly proceeds when the treated thin-layer rod is immersed in an anhydrous solution containing trimethylmonochlorosilane dissolved in an organic solvent such as toluene or dioxane in a concentration of 10% and then refluxed for about two hours. Although the aforementioned hydrolysis can be attained by the use of a dilute acid or a dilute alkali of course, it is generally sufficient to treat with water. Subsequently, the thin-layer rod which has undergone the treatments is washed with an organic solvents such as toluene or dioxane. Desirably, it is further washed with a solvent such as methanol or acetone for the purpose of facilitating desired removal of adhering water and the solvent used. Thereafter, the thin-layer rod is thoroughly dried, for example, by being heated at 130° C. for several hours. In the thin-layer rod thus obtained has its stationary phase chemically modified throughout the entire length thereof. The thin-layer rod in this state is not conveniently used for FID-TLC. The thin-layer rod contemplated by the present invention is obtained as by having the portion thereof corresponding to the detection part calcined at an elevated temperatures thereby converting this portion into the original thin layer of adsorbent. In the aforementioned reaction, where the subscript n of formula (I) is 2 or 3, there are times when one molecule of the organic silane as the chemical modifier may react with a plurality of hydroxyl groups or silanol groups of adsorbents or the unreacted portion of the substituent X may react with some of the remaining molecules of the organic silane and gives birth to a complicated structure.

The chemical modification which comprises treating the stationary phase of the thin-layer rod with a halogenating agent and subsequently treating it with a Grignard reagent or an organic lithium compound or an organic amine can be carried out, for example, as follows. The thin-layer rod is immersed in an anhydrous organic solvent such as pentane having thionyl chloride, silicon chloride, or titanium chloride dissolved in advance therein and the immersed thin-layer rod is refluxed for chlorination for about 1 hour. Then, a Grignard reagent represented by formula RMgCl, an organic lithium compound represented by formula RLi, or an organic amine represented by formula $RNH_2$ is added thereto and allowed to react thoroughly therewith. After completion of the reaction, the treated thin-layer rod is thoroughly washed with a solvent, for example, with water, ether, chloroform, and acetone, in the order listed. Finally, the portion of the thin-layer rod corresponding to the detection part is selectively converted to the original layer of adsorbent by the method such as by being calcined at elevated temperature, etc.

As clearly noted from the foregoing detailed description, the thin-layer rod which has had the stationary phase chemically modified throughout the entire length thereof is an intermediate for a thin-layer rod (final product) which has the development starting side thereof chemically modified and the remaining portion thereof equaling the stationary phase of the conventional thin-layer rod. The chromatographic thin-layer rod of the present invention embraces both versions. In the case of the thin-layer rod having the stationary phase chemically modified throughout the entire length thereof, the work of baking only the portion thereof corresponding to the detection part thereby converting the portion into the original layer of adsorbent can be easily carried out not only in the factory operated for the manufacture of the thin-layer rods but also in the laboratory engaged in the analysis by the use of the thin-layer rod. The work of baking in the laboratory can be carried out by using an FID or a furnace.

The thin-layer rod of the present invention, in spite of simple construction and easy fabrication, enjoys the advantage that it provides highly satisfactory separation and warrants the precision required quantitative analysis. It manifests a salient effect of easily and accurately performing separation and determination of hydrocarbons, especially high boiling polycyclic aromatic hydrocarbons with respect to which the conventional thin-layer rod has effected separation and determination only with difficulty. It particularly enables monocyclic aromatic hydrocarbons, bicyclic aromatic hydrocarbons, and tricyclic aromatic hydrocarbons to be severally determined easily and accurately.

In the working examples cited below, the thin-layer rod of the present invention and the conventional countertype are compared with respect to their performance manifested in the separation of aromatic hydrocarbons, thus demonstrating the effects of the present invention.

In each of the working examples cited below, the thin-layer chromatography was conducted by the following procedure.

At the origin of a given thin-layer rod, a sample toluene solution prepared in a prescribed concentration (10 wt %) is spotted in a volume of 1.0 μl. The thin-layer rod is suspended for 10 minutes in an atmosphere of vapour of a prescribed developing solvent in a closed developing tank, and then the lower part (the development starting side) of the thin-layer rod is immersed in the solvent liquid in the developing tank for enabling the development to advance to the leading end point thereof. The thin-layer rod is dried in a draft chamber at room temperature. The dry thin-layer rod is subjected to detection in an FID to obtain a chromatogram, from which the $R_f$ value, the half-value width, and the degree of separation are found. In an experiment performed on a fixed volume of a given sample, freedom from the obscurity of image increases in proportion as the half-value width decreases. The degree of separation ($R_s$) is calculated in accordance with the following formula.

$$R_s = \frac{|(Z_x)_2 - (Z_x)_1|}{(b_2 + b_1)}$$

wherein $(Z_x)_1$ and $(Z_x)_2$ represents the distances from the origin to the peaks of the component 1 and the component 2 respectively and $b_1$ and $b_2$ represents the half-value width of the two components mentioned above, i.e., the withds of the peaks at the values corresponding to 50% of the maximum values of the peaks in question. This formula denotes that the clarity of separation between two components increases in proportion as the degree of separation ($R_s$) increases.

The detection with the FID was conducted only in the detection part of each of the thin-layer rods according to this invention and throughout the entire length of each of the conventional thin-layer rods.

EXAMPLE 1 AND COMPARATIVE EXPERIMENTS 1–2

A commercially available silica gel thin-layer rod produced by forming a deposition, by baking silica gel onto a quartz glass rod (product of Iatron laboratories, Inc.), was chemically modified as follows. The commercially available silica gel thin-layer rod was immersed in a solution of 3-amino-propyltriethoxysilane in toluene and refluxed therein for 10 hours. The resultant silica gel thin-layer rod was washed with toluene and then washed with methanol. Subsequently, the silica gel thin-layer rod consequently obtained was dried at 130° C. for 5 hours, to obtain a chemically modified thin-layer rod. Then, a portion 60% of the entire length of this thin-layer rod was baked with a flame ionization detector so as to be converted to the original stationary phase of silica gel.

By the use of the thin-layer rod having the separation part and the detection part formed therein in a ratio of 4/6 prepared by using 3-aminopropyltriethoxysilane as a chemical modifier (Example 1), a commercially available silica gel thin-layer rod which had not undergone any chemical modification (Comparative Experiment 1), and a commercially available alumina thin-layer rod which had not undergone any chemical modification (Comparative Experiment 2), a monocyclic, a bicyclic, and a tricyclic aromatic hydrocarbon indicated in Table 1 were subjected by the procedure described above to chromatography using n-hexane as a developing solvent, to find the $R_f$ value, the half-value width, and the degree of separation. The results were as shown in Table 1.

Here, $R_{s1}$ represents the degree of separation between monocyclic aromatic hydrocarbons and bicyclic aromatic hydrocarbons and $R_{s2}$ represents the degree of separation between bicyclic aromatic hydrocarbons and tricyclic aromatic hydrocarbons.

TABLE 1

|  | Example 1 | Comparative Experiment 1 | Comparative Experiment 2 |
|---|---|---|---|
| Compound A: |  |  |  |
| $R_f$ value | 0.70 | 0.57 | 0.66 |
| Half-value width | 0.053 | 0.098 | 0.100 |
| Compound B: |  |  |  |
| $R_f$ value | 0.58 | 0.40 | 0.59 |
| Half-value width | 0.070 | 0.112 | 0.092 |
| Compound C: |  |  |  |
| $R_f$ value | 0.45 | 0.29 | 0.42 |
| Half-value width | 0.052 | 0.120 | 0.090 |
| $R_{s1}$ | 0.98 | 0.81 | 0.36 |
| $R_{s2}$ | 1.07 | 0.47 | 0.93 |

Compound A: n-Dodecylbenzene
Compound B: 2,6-Dimethyl naphthalene
Compound C: Anthracene It is noted from the Table 1 that the separation between the monocyclic and bicyclic aromatic hydrocarbons and the separation between the bicyclic and tricyclic aromatic hydrocarbons were separated more satisfactorily in Example 1 than in Comparative Experiments 1 and 2.

EXAMPLE 2 AND COMPARATIVE EXPERIMENTS 3–4

By the use of a thin-layer rod having a separation part and a detection part formed in a proportion of 4/6 prepared by using 3-amino-propyltriethoxysilane as a chemical modifier and following the same procedure of Example 1, except that dioxane was used in place of toluene as a solvent (Example 2), a commercially available silica gel thin-layer rod which had not undergone any chemical modification (Comparative Experiment 3), and a commercially available alumina thin-layer rod which had not undergone any chemical modification (Comparative Experiment 4), a monocyclic, a bicyclic, and a tricyclic aromatic hydrocarbon indicated in Table 2 were subjected to chromatography by following the procedure described above using n-hexane as a solvent, to find the $R_f$ value, the half-value width, and the degree of separation. The results were as shown in Table 2.

Here, $R_{s1}$ represents the degree of separation between monocyclic aromatic hydrocarbons and bicyclic aromatic hydrocarbons and $R_{s2}$ represents the degree of separation between bicyclic aromatic hydrocarbons and tricyclic aromatic hydrocarbons.

TABLE 2

|  | Example 2 | Comparative Experiment 3 | Comparative Experiment 4 |
|---|---|---|---|
| Compound D: |  |  |  |
| $R_f$ value | 0.71 | 0.57 | 0.68 |
| Half-value width | 0.060 | 0.100 | 0.101 |
| Compound E: |  |  |  |
| $R_f$ value | 0.56 | 0.45 | 0.57 |
| Half-value width | 0.062 | 0.102 | 0.096 |
| Compound F: |  |  |  |
| $R_f$ value | 0.44 | 0.26 | 0.43 |
| Half-value width | 0.064 | 0.138 | 0.088 |
| $R_{s1}$ | 1.23 | 0.59 | 0.56 |
| $R_{s2}$ | 0.95 | 0.79 | 0.76 |

Compound D: n-octadecyl benzene
Compound E: Acenaphthene
Compound F: 9,10-Dimethyl anthracene It is noted from the Table 2 that the thin-layer rod of the present invention (Example 2) showed better performance in the separation between the monocyclic and bicyclic aromatic hydrocarbons and the separation between the bicyclic and tricyclic aromatic hydrocarbons than the conventional thin-layer rods (Comparative Experiments 3-4).

EXAMPLE 3

By the use of a thin-layer rod having a separation part and a detection part formed in a ratio of 4/6 prepared by following the procedure of Example 1, except that 3-cyano-propyltrichlorosilane was used as a chemical modifier in the place of 3-amino-propyltriethoxysilane, monocyclic, bicyclic, and tricyclic aromatic hydrocarbons indicated in Tables 3 and 4 were subjected to chromatography using the same sample solution as used in Examples 1 and 2, and using n-hexane as a developing solvent, to find the $R_f$ value, the half-value width, and the degree of separation. The results were as shown in Table 3 and Table 4. In this experiment, the same clear separation of monocyclic, bicyclic, and tricyclic aromatic hydrocarbons was obtained as in Example 1.

Here, $R_{s1}$ represents the degree of separation between monocyclic aromatic hydrocarbons and bicyclic aromatic hydrocarbons and $R_{s2}$ represents the degree of separation between bicyclic aromatic hydrocarbons and tricyclic aromatic hydrocarbons.

TABLE 3

| n-Dodecyl benzene | $R_f$ value | 0.75 |
|---|---|---|
|  | Half-value width | 0.080 |
| 2,6-Dimethylnaphtahalene | $R_f$ value | 0.59 |
|  | Half-value width | 0.078 |
| Anthracene | $R_f$ value | 0.49 |
|  | Half-value width | 0.045 |
| $R_{s1}$ |  | 1.01 |
| $R_{s2}$ |  | 0.81 |

TABLE 4

| n-Octadecyl benzene | $R_f$ value | 0.75 |
|---|---|---|
|  | Half-value width | 0.080 |
| Acenaphthene | $R_f$ value | 0.62 |
|  | Half-value width | 0.067 |
| 9,10-Dimethyl anthracene | $R_f$ value | 0.48 |
|  | Half-value width | 0.046 |
| $R_{s1}$ |  | 0.88 |
| $R_{s2}$ |  | 1.24 |

In a separate experiment conducted by the use of thin-layer rods produced by using silane compounds of formula (I) containing —$NO_2$, —$SO_3H$, and —COOH groups as chemical modifiers, as clear separation of monocyclic, bicyclic, and tricyclic aromatic hydrocarbons was attained as in Examples 1-3.

EXAMPLE 4

In a solution having n-octyldimethylmonochlorosilane dissolved in toluene as a solvent, a commercially available silica gel thin-layer rod having silica gel deposited fast thereon by baking (product of Iatron Laboratory, Inc.) was immersed and refluxed for 10 hours. The resultant thin-layer rod was washed with toluene, and then thoroughly washed with methanol. In a solution containing trimethylmonochlorosilane dissolved in toluene in a concentration of 10%, the resultant thin-layer rod was immersed and refluxed for 2 hours. Subsequently, the thin-layer rod was washed first with toluene and then with methanol and dried at 130° C. for 5 hours, to obtain a chemically modified thin-layer rod. The portion 60% of the entire length of this thin-layer rod was baked with a flame ionization detector so as to be converted to the original stationary phase of silica gel.

By the use of the thin-layer rod having the separation part and the detection part formed in a ratio of 4/6 prepared by using n-octyl-dimethylmonochlorosilane as a chemical modifier, bicyclic, tricyclic, and tetracyclic aromatic hydrocarbons indicated in Table 5 were subjected to chromatography by following the procedure described above and using a methanol/water (70/30 by volume) mixture as a developing solvent, to find the $R_f$ value, the half-value width, and the degree of separation. The results were as shown in Table 5. In this experiment, the clear separation of bicyclic, tricyclic, and tetracyclic aromatic hydrocarbons was attained and separation between two tetracyclic compounds was attained to a considerably high degree.

Here, $R_{s1}$ represents the degree of separation between naphthalene and phenanthrene, $R_{s2}$ represents the degree of separation between phenanthrene and pyrene, and $R_{s3}$ represents the degree of separation between pyrene and chrysene.

TABLE 5

| Naphthalene | $R_f$ value | 0.82 |
|---|---|---|
|  | Half-value width | 0.050 |
| Phenanthrene | $R_f$ value | 0.60 |
|  | Half-value width | 0.046 |
| Pyrene | $R_f$ value | 0.48 |
|  | Half-value width | 0.046 |
| Chrysene | $R_f$ value | 0.42 |
|  | Half-value width | 0.044 |
| $R_{s1}$ |  | 2.29 |
| $R_{s2}$ |  | 1.30 |
| $R_{s3}$ |  | 0.67 |

In a separate experiment conducted by the use of thin-layer rod produced by using a silane compound of formula (I) containing a varying n-alkyl group or phenyl group, as clear a separation of polycyclic aromatic hydrocarbons as in Example 4 was obtained.

EXAMPLES 5-6 AND COMPARATIVE EXPERIMENTS 5-6

As representatives of the monocyclic, bicyclic, and tricyclic aromatic hydrocarbons, n-octadecyl benzene, 2,6-dimethyl naphthalene, and 9,10-dimethyl anthracene were selected. Their standard mixed samples were prepared. By the use of various thin-layer rods, these mixed samples were subjected to chromatography, to find the degrees of separation, $R_{s1}$ and $R_{s2}$, between the two sets of adjoining components. The results were as shown in Table 6.

Comparative Experiment 5 used a commercially available silica gel thin-layer rod, Comparative Experiment 6 used a commercially available alumina thin-layer rod, Example 5 used the same thin-layer rod as used in Example 1, and Example 6 used the same thin-layer rod as used in Example 3. n-Hexane was invariably used as a developing solvent.

It is noted from Table 6 that the values of $R_{s1}$ and $R_{s2}$ were low in the case of the commercially available silica gel and alumina thin-layer rods, whereas they were high in the case of the thin-layer rods according to the present invention. The comparison shows that the thin-layer rods of this invention excelled in their separating properties.

TABLE 6

| Kind of thin-layer rod | | Degree of separation | |
| --- | --- | --- | --- |
| | | $R_{s1}$ | $R_{s2}$ |
| Comparative Experiment 5 | Commercially available silica gel thin-layer rod | 0.80 | 0.56 |
| Comparative Experiment 6 | Commercially available alumina thin-layer rod | 0.47 | 0.89 |
| Example 5 | Thin-layer rod used in Example 1 | 1.00 | 1.04 |
| Example 6 | Thin-layer rod used in Example 3 | 1.01 | 0.89 |

Figure 2A:
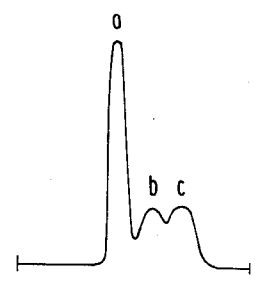
FIGS. 2A and 2B, FIG. 3, and FIG. 4 show chromatograms obtained by the analysis of samples by the thin-layer chromatographic method using a flame ionization detector (FID-TLC). In each of the graphs, the abscissa represents the scale of the length on the thin-layer rod and the point O on the abscissa represents the origin (the point for starting the development of a sample) and the point F on the abscissa represents the leading end point (the point of the leading end of a solvent used in the development of the sample), whereas the ordinate represents the scale of the relative strength of detection (FID response).
Figure 2B:
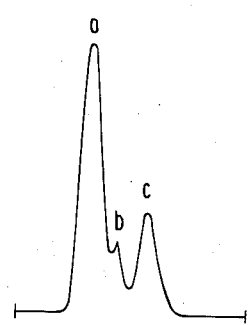
Figure 3:
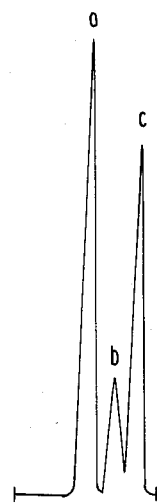
Figure 4:
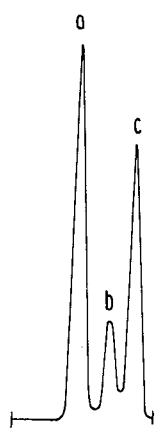

The chromatogram obtained in Comparative Experiment 5 is shown by Curve A and that in Comparative Experiment 6 by Curve B respectively in FIG. 2 and that in Example 5 in FIG. 3, and that in Example 6 in FIG. 4. In the diagrams, "a" represents the peak of n-octadecyl benzene, "b" represents the peak of 2,6-dimethyl naphthalene, and "c" represents the peak of 9,10-dimethyl anthracene.

While the invention has been described in detail and with reference to specific embodiments thereof, it will be apparent to one skilled in the art that various changes and modifications can be made therein without departing from the spirit and scope thereof.

What is claimed is:

1. A method for the thin-layer chromatographic separation of a test sample containing a mixture of organic compounds, which comprises developing and separating said test sample on a thin-layer rod for thin-layer chromatography using a developing solvent, said thin-layer rod comprising a rod-like support and a stationary phase made of an adsorbent which is superposed on said rod-like support, with chemical modification made in part of said stationary phase to effect affinity chromatography and provide a high degree of separation, the chemically modified stationary phase being placed on a lower separation part of the thin-layer rod, and after separation, determining by use of a flame ionization detector the separated component on an upper detection part of the thin-layer rod which is not chemically modified.

2. A method according to claim 1, wherein said chemical modification is conducted by treatment with an organic silane.

3. A method according to claim 2, wherein said organic silane is a halogenated organic silane or an organic alkoxysilane.

4. A method according to claim 3, wherein said organic silane is represented by formula (I)

$$X_nSiR'_{3-n}-R \quad (I)$$

wherein X represents a halogen atom or an alkoxyl group, n represents 1, 2, or 3, R' represents a lower alkyl group, and R represents a monovalent hydrocarbon group or a monovalent polar group-substituted hydrocarbon group.

5. A method according to claim 4, wherein X represents a chlorine atom, methoxy group, or ethoxy group, and R' represents methyl group or ethyl group, and said group R represents an alkyl group, an alkenyl group, an aromatic group-substituted alkyl group, an aromatic group, an amino-alkyl group, a cyano-alkyl group, a nitro-alkyl group, a sulfo-alkyl group, a carboxy-alkyl group, or a nitro-aromatic group.

6. A method according to claim 5, wherein said group R represents methyl, ethyl, n-butyl, n-octyl, n-octadecyl, phenethyl, phenyl, 3-aminopropyl, 3-cyanopropyl, 3-nitropropyl, 3-sulfopropyl, 3-carboxypropyl, or nitrophenyl group.

7. A method according to claim 1, wherein said chemical modification is conducted by a treatment with a halogenating agent and a subsequent treatment with a Grignard reagent represented by the formula RMgCl, an organic lithium represented by the formula RLi, or an organic amine represented by the formula RLi, or an organic amine represented by the formula $RNH_2$, wherein R represents a monovalent hydrocarbon group or a monovalent polar group-substituted hydrocarbon group.

8. A method according to claim 7, wherein R represents an alkyl group, an alkenyl group, an aromatic group-substituted alkyl group, an aromatic group, an amino-alkyl group, a cyano-alkyl group, a nitro-alkyl group, a sulfo-alkyl group, a carboxy-alkyl group, or a nitro-aromatic group.

9. A method according to claim 8, wherein R represents methyl, ethyl, n-butyl, n-octyl, n-octadecyl, phenethyl, phenyl, 3-aminopropyl, 3-cyanopropyl, 3-nitropropyl, 3-sulfopropyl, 3-carboxypropyl, or nitrophenyl group.

10. A method according to claim 1, wherein said chemically modified part comprises from 10 to 70% of the entire length of said stationary phase.

11. A method according to claim 1, wherein said rod-like support is a rod-like member made of quartz, glass, or ceramic.

12. A method according to claim 1, wherein said adsorbent is silica gel, alumina, porous glass powder, diatomaceous earth, or magnesium silicate.

13. A method according to claim 1 wherein said chemically modified part comprises from 30 to 60% of the entire length of said stationary phase.

* * * * *